United States Patent
Snyder et al.

(10) Patent No.: US 7,708,960 B2
(45) Date of Patent: May 4, 2010

(54) DRY HEAT CONVECTION STERILIZATION SYSTEM

(75) Inventors: Gary C. Snyder, Montoursville, PA (US); Robert L. Sholes, Williamsport, PA (US)

(73) Assignee: SPX Corporation, Charlotte, NC (US)

( * ) Notice: Subject to any disclaimer, the term of this patent is extended or adjusted under 35 U.S.C. 154(b) by 876 days.

(21) Appl. No.: 11/393,759

(22) Filed: Mar. 31, 2006

(65) Prior Publication Data

US 2007/0237670 A1  Oct. 11, 2007

(51) Int. Cl.
*A61L 2/04* (2006.01)
*A61K 39/02* (2006.01)
*A61L 2/00* (2006.01)
*A61L 9/00* (2006.01)
*A61L 11/00* (2006.01)

(52) U.S. Cl. .................. 422/307; 422/243; 422/292; 422/1

(58) Field of Classification Search .................. 422/295; 454/306; 56/13.1
See application file for complete search history.

(56) References Cited

U.S. PATENT DOCUMENTS

| | | | | |
|---|---|---|---|---|
| 2,251,617 A | * | 8/1941 | Pirnie | 34/467 |
| 2,370,422 A | * | 2/1945 | Reed | 34/193 |
| 3,496,704 A | * | 2/1970 | Bandlow | 96/138 |
| 4,481,871 A | * | 11/1984 | Efstratis | 454/306 |
| 4,625,432 A | * | 12/1986 | Baltes | 34/621 |
| 4,974,663 A | * | 12/1990 | Nakaji | 165/61 |
| 5,079,855 A | * | 1/1992 | Carrier | 34/225 |
| 5,439,643 A | | 8/1995 | Liebert | |
| 5,525,295 A | | 6/1996 | Pflug et al. | |
| 5,680,712 A | * | 10/1997 | Kiyokawa et al. | 34/267 |
| 5,849,246 A | | 12/1998 | Hashimoto et al. | |
| 6,174,231 B1 | * | 1/2001 | Bodin | 454/184 |
| 6,383,449 B1 | | 5/2002 | Pennekamp et al. | |
| 6,478,369 B1 | * | 11/2002 | Aoki et al. | 297/180.13 |
| 6,511,372 B2 | * | 1/2003 | Leeds et al. | 454/186 |
| 6,797,930 B2 | * | 9/2004 | Kim | 219/757 |

* cited by examiner

*Primary Examiner*—Elizabeth L McKane
*Assistant Examiner*—Regina Yoo
(74) *Attorney, Agent, or Firm*—Baker & Hostetler LLP

(57) ABSTRACT

A dry heat sterilization system having a housing and a number of plenums to guide the flow of hot air. Hot air is forced to flow through the plenums, the intake slide duct and into the bottom of the containers. The hot air will rise and exit from the top of the container through the exhaust slide duct. Furthermore, the external surfaces of the container are also sterilized through the use of semi-pierced duct walls with adjustable diffuser panels. Hot air will re-circulate until it reaches a pre-determined temperature. The container and its contents can be safely handled once the exhaust air blower removes hot air from the system.

23 Claims, 6 Drawing Sheets

DRY HEAT CONVECTION STERILIZATION SYSTEM

FIELD OF THE INVENTION

The present invention relates generally to a sterilization system. More particularly, the present invention relates to a sterilization system using dry heat.

BACKGROUND OF THE INVENTION

Traditionally, steam is a common way to sterilize cages and other contaminants. A widely-used device for heat sterilization is the autoclave. Autoclave commonly use steam heated to 121° C. (250° F.), at 103 kPa (15 psi) above atmospheric pressure to transfer sufficient heat to sterilize the content. For effective autoclaving, the steam needs to be able to penetrate the entire device. For this reason, an autoclave must not be overcrowded, and the lids of bottles and containers must be ajar. Furthermore, indicators must be placed in the most difficult place to sterilize to ensure that steam actually penetrates these areas.

Unfortunately, the use of steam autoclaves bears high initial cost, high operating cost (steam boiler, distribution lines, high volumes or water, and licensing of operators), and high maintenance costs. Furthermore, the user of the steam autoclaves must allow the steam to cool down to ambient liquid form before disposing to the drain.

Accordingly, it is desirable to provide a sterilization system using dry heat convection. The use of a dry heat convection sterilizer eliminates the high initial costs, operating costs and maintenance costs of sterilization via the autoclave. Furthermore, the use of dry heat convection sterilizer benefits the environment because hot steams will not be released from the system into the environment.

SUMMARY OF THE INVENTION

The foregoing needs are met, to a great extent, by the present invention, wherein in one aspect an apparatus is provided that in some embodiments the heated air is introduced directly into the enclosed, sealed container at the bottom side wall and exhausted at the top of the opposite side wall. Furthermore, the external surfaces of the container are being heated by convected air from the outside.

In accordance with one embodiment of the present invention, a sterilization system using hot air, including a housing having a ceiling with an airflow inlet and an airflow outlet, a first side wall coupled to the ceiling, and a second side wall coupled to the ceiling, such that a chamber is formed; a first plenum substantially adjacent to the first side wall; a second plenum substantially adjacent to the first plenum; a third plenum substantially adjacent to the second side wall; a deflector mounted inside the chamber, such that the deflector directs air between the first and second plenums; an intake slide duct slidably attached to the first side wall, such that the intake slide duct penetrates through the first side wall, the first plenum, and the second plenum into the chamber; and an exhaust slide duct slidably attached to the second side wall, such that the exhaust slide duct penetrates through the second side wall and the third plenum into the chamber. The sterilization system further including semi-pierced duct walls mounted inside the chamber, such that the intake slide duct and the exhaust slide duct penetrate through the semi-pierced duct walls, wherein the semi-pierced duct walls further comprises adjustable diffuser panels. The intake slide duct further having an opening at the end of the intake slide duct, an air turning vane, and apertures on the top of the slide duct, such that when air enters from the top of the intake slide duct, the air turning vane guides the airflow, thereby the air enters into the chamber through the opening. The exhaust slide duct further having an opening at the end of the exhaust slide duct and apertures on both top and bottom of the slide duct, such that air can enter into the slide duct from the opening or the bottom apertures and exit through the top apertures. The intake slide duct is relatively lower than the exhaust slide duct, thereby hot air will enter through the intake slide duct, rise to the top of the chamber and exit through the exhaust slide duct. The sterilization system further including an intake filter box mounted on the ceiling; an intake air blower coupled to the intake filter box and mounted on the ceiling, wherein the intake air blower directs air to flow from the filter box through the airflow inlet and into the chamber; a re-circulating air blower mounted under the ceiling and inside the chamber to re-circulate air; and a heater mounted between the intake air blower and the re-circulating air blower, such that the air is heated when it enters the re-circulating air blower from the intake air blower. The sterilization system further having an exhaust filter box mounted on the ceiling; and an exhaust air blower coupled to the exhaust filter box and mounted on the ceiling, wherein the exhaust air blower directs air to flow from the chamber through the airflow outlet and into the exhaust filter box.

In accordance with another embodiment of the present invention, an apparatus for sterilization using air, including a housing means having a ceiling with an airflow inlet and an airflow outlet, a first side wall coupled to the ceiling, and a second side wall coupled to the ceiling, such that a chamber is formed; a first airflow means substantially adjacent to the first side wall; a second airflow means substantially adjacent to the first airflow means; a third airflow means substantially adjacent to the second side wall; a deflector means mounted inside the chamber, such that the deflector means directs air between the first and second airflow means; an intake duct means slidably attached to the first side wall, such that the intake slide duct penetrates through the first side wall, the first airflow means and second airflow means into the chamber; and an exhaust duct means slidably attached to the second side wall, such that the exhaust slide duct penetrates through the second side wall and the third airflow means into the chamber. The apparatus further including semi-pierced barrier means mounted inside the chamber, such that the intake duct means and the exhaust duct means penetrate through the semi-pierced barrier means, wherein the semi-pierced barrier means further comprises adjustable diffuser panels. The intake duct means further comprises an opening at the end of the intake duct means, an air turning vane, and apertures on the top of the intake duct means, such that when air enters from the top of the intake duct means, the air turning vane guides airflow, thereby the air enters into the chamber through the opening. The exhaust duct means further comprises an opening at the end of the exhaust duct means and apertures on both top and bottom of the exhaust duct means, such that air can enter into the slide duct from the opening or the bottom apertures and exit through the top apertures. The intake duct means is relatively lower than the exhaust duct means, thereby hot air entering through the intake duct means, rising to the top of the chamber and exiting through the exhaust slide duct.

In accordance with yet another embodiment of the present invention, a method for using a dry air convection sterilizer, including the steps of ramping the sterilizer from ambient temperature to a set point temperature; heating the sterilizer at the set point temperature for a desired period of time; and cooling the sterilizer to about 140° F. The method further including placing a container inside the sterilizer; penetrating the container with an intake slide duct and an exhaust slide duct; and circulating hot air inside and around the container.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
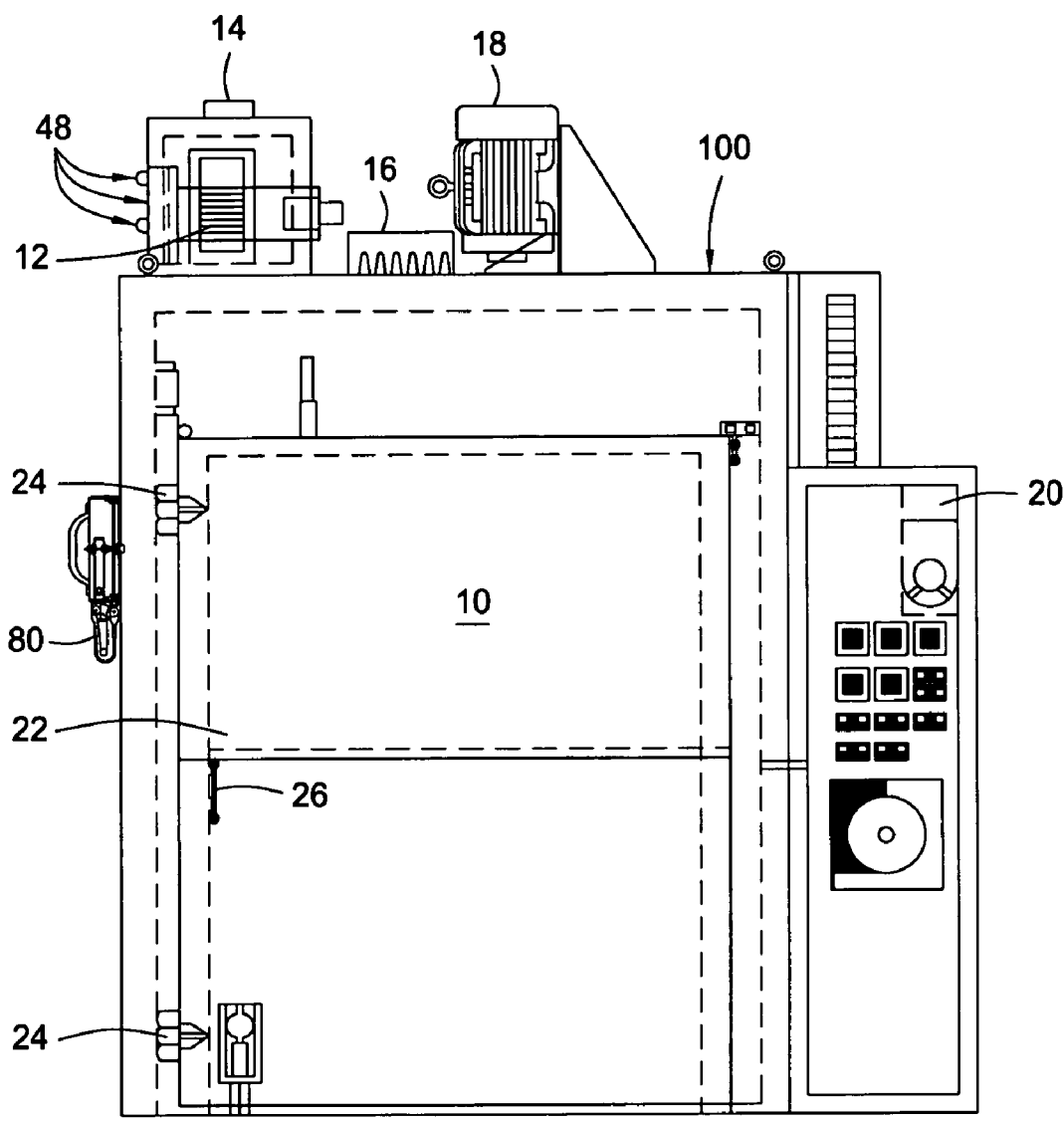
FIG. 1 is a front view illustrating a sterilization system according to an embodiment of the invention.

The invention will now be described with reference to the drawing figures, in which like reference numerals refer to like parts throughout. An embodiment in accordance with the present invention provides a sterilization system utilizing dry heat convection. The sterilizer having a housing and a number of plenums to guide the flow of hot air. Hot air is forced to flow though the plenums, an intake slide duct and into the bottom of a container being sterilized. The hot air will rise and exit from the top of the container through an exhaust slide duct. Furthermore, the external surfaces of the container are also sterilized through the use of a semi-pierced duct wall with adjustable diffuser panels. Hot air will re-circulate until it reaches a pre-determined temperature. The container and its contents can be safely handled once an exhaust air blower removes hot air from the system.

Figure 2:
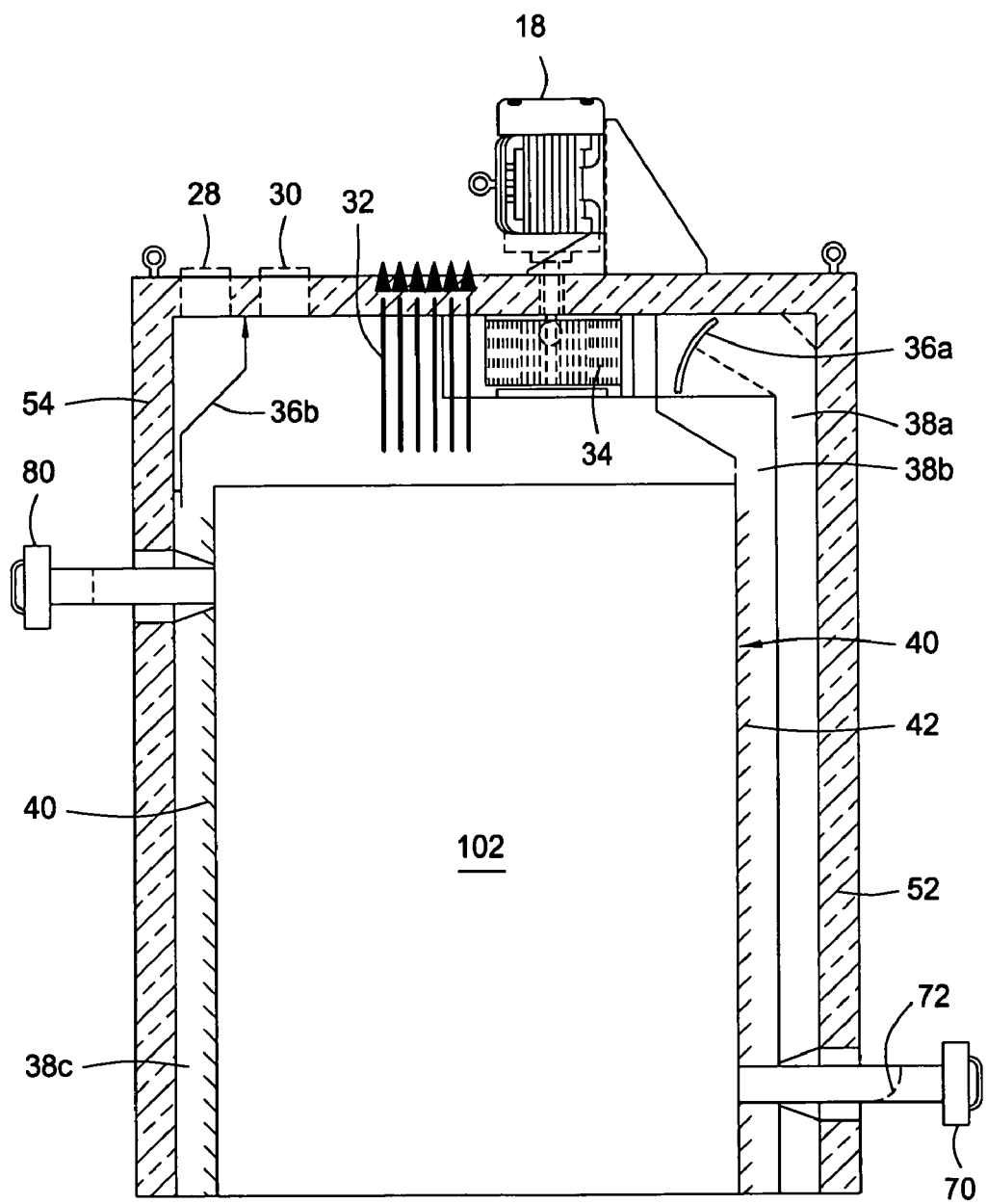
FIG. 2 is a cutaway view of the sterilization system of FIG. 1.

FIG. 1 is a front view illustrating a sterilization system 10 according to an embodiment of the invention. As shown in FIG. 1, the sterilization system 10 has a housing 100, an intake airflow blower 12, an intake filter box 14, an exhaust filter box 44 (FIG. 3), an exhaust airflow blower 46 (FIG. 4), an electrical junction box 16, a re-circulating motor 18, a door 22 with two latches 24 and a handle 26, a control console 20, an exhaust slide duct 80, and an intake slide duct 70 (FIG. 2). The intake airflow blower 12, the intake filter box 14, the electrical junction box 16, and the re-circulating motor 18 can be mounted on top of the housing 100. Alternatively, these parts can also be mounted on the side of the housing 100.

In operation, the control console 20 has controllers and recorders for controlling and recording the temperature of the sterilization cycle. The control console 20 also has various buttons and indicators for controlling the sterilization systems such as, for example, start button, stop button, fault indicator, temperature display, timer, alarm, etc.

Figure 3:
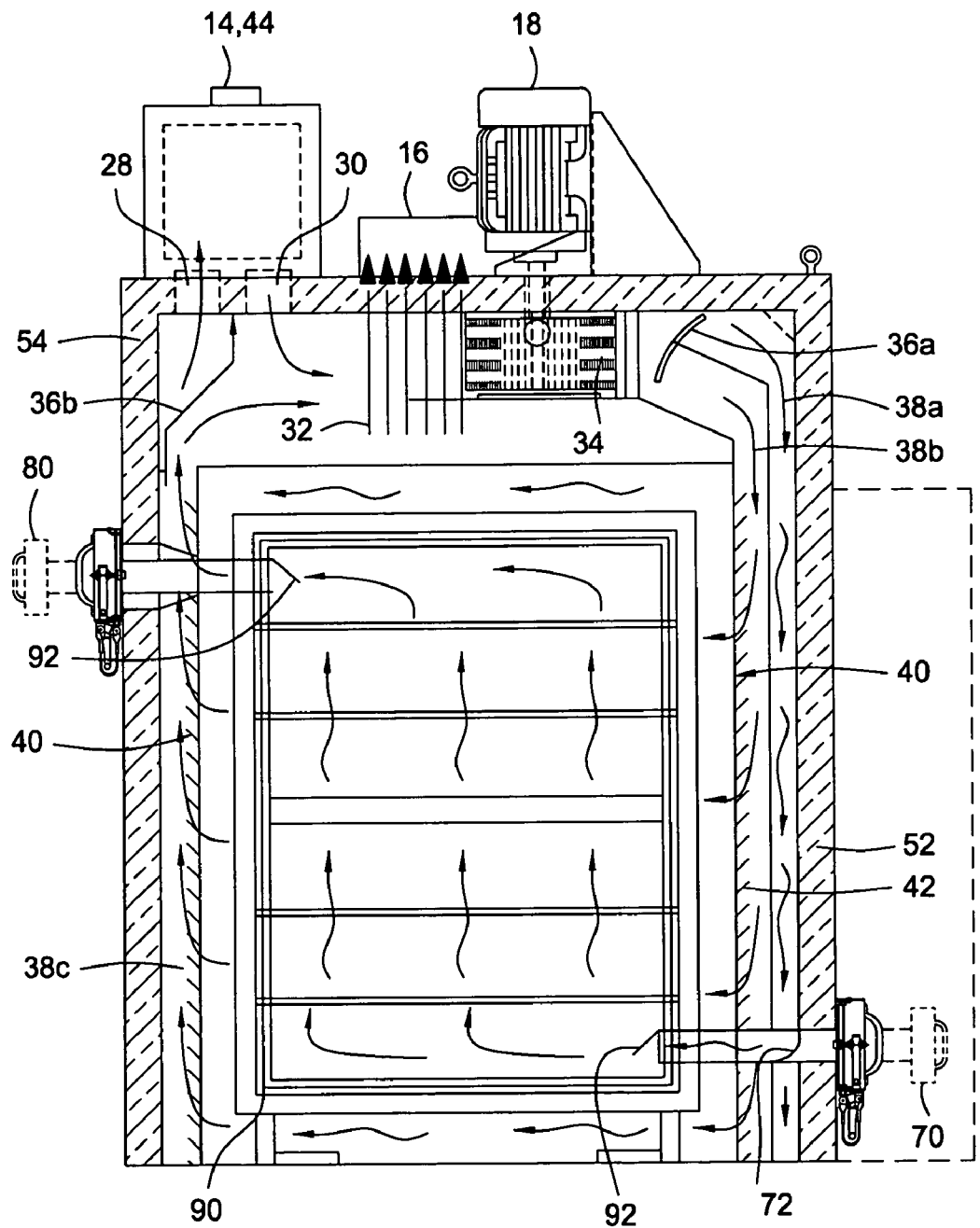
FIG. 3 is another cutaway view of the sterilization system of FIG. 1 showing airflow.

In the present embodiment, the sterilization system 10 has two identical filters located within the intake filter box 14 and the exhaust filter box 44 (FIG. 3). An intake filter cleans air as the air is directed into the chamber from the atmosphere, while the exhaust filter ensures that containments in the chamber is contained in the exhaust filter box 44 and not released into the atmosphere when the hot air is vented. Furthermore, another function of the filters is to prevent ambient air from entering the chamber through the exhaust outlet to re-contaminate the contents when the sterilization process is complete.

As indicated, the intake filter box 14 and the exhaust filter box 44 each contains high efficiency filters including, for example, HEPA filters. Furthermore, ports 48 on the intake filter box 14 are used to introduce test materials to test the integrity of the intake filter box 14. Similarly, exhaust filter box 44 (FIG. 3) also has ports for similar purposes. The ports 48 check the upstream and downstream of the airflow of the filters to ensure that the filter box 14 is functioning properly. For example, an operator can confirm that there is no leakage in the system or any obstruction of airflow in the filter. There is a set of three ports: an intake input port, an intake scan port and an intake 100% test port. In operation, a test material is introduced through the intake input port, and a sensor in the port will verify the concentration of the material. Then, another probe is placed in the intake scan port, which is downstream to the intake input port, to measure the concentration of the material that passed through the filter. If the filter scan test failed, an attempt is made to correct the problem. For example, the operator can increase the clamp force on the filter gasket or seal any small leak in the filter media with silicon caulk. If these measures are not successful, a new filter will be installed.

In another embodiment, the sterilization system can have one or more filters depending on the user's specification and application. In situations where the users are located in a class 100 atmosphere, an intake filter might not be necessary. In that situation, the production cost of manufacturing the sterilization system will decrease. Nonetheless, an exhaust filter can prevent ambient air from re-entering and contaminating the chamber 102 (FIG. 2).

The intake airflow blower 12 is attached to the intake filter box 14 and has a mechanism that forces air into the chamber 102 (FIG. 2). Furthermore, the exhaust airflow blower 46 is attached to the exhaust filter box 44 and pulls air through the filter box and exhaust air into the atmosphere away from the housing.

FIG. 2 is a cutaway view of the sterilization system 10 showing the chamber 102 of the sterilization system 10. The sterilization system 10 has an air intake wall 52, an air exhaust wall 54, a first plenum 38a substantially adjacent to the air intake wall 52, a second plenum 38c substantially adjacent to the air exhaust wall 54.

In another embodiment, the sterilization system 10 can have a third plenum 38c substantially adjacent to the first plenum 38a. Furthermore, a deflector 36a is located between the first plenum 38a and the third plenum 38b, such that the deflector 36a distributes air to flow down the first plenum 38a and the third plenums 38b.

The sterilization system 10 also has a set of semi-pierced duct walls 40 inside the chamber 102. The semi-pierced duct walls 40 have numerous adjustable diffuser panels 42. In operation, the diffuser panels are angled in such a way that they aid the airflow in and out of the chamber 102. These diffuser panels are adjustable according to the needs of the user and the contents being sterilized in the system.

An intake slide duct 70, having an air turning vane 72, is slidably attached near the bottom of the sterilization system 10 and penetrates the air intake wall 52, the first plenum 38a and the third plenum 38b. Similarly, the exhaust slide duct 80 is slidably attached near the top of sterilization system 10 and penetrates the air exhaust wall 54 and the second plenum 38c.

Figure 4:
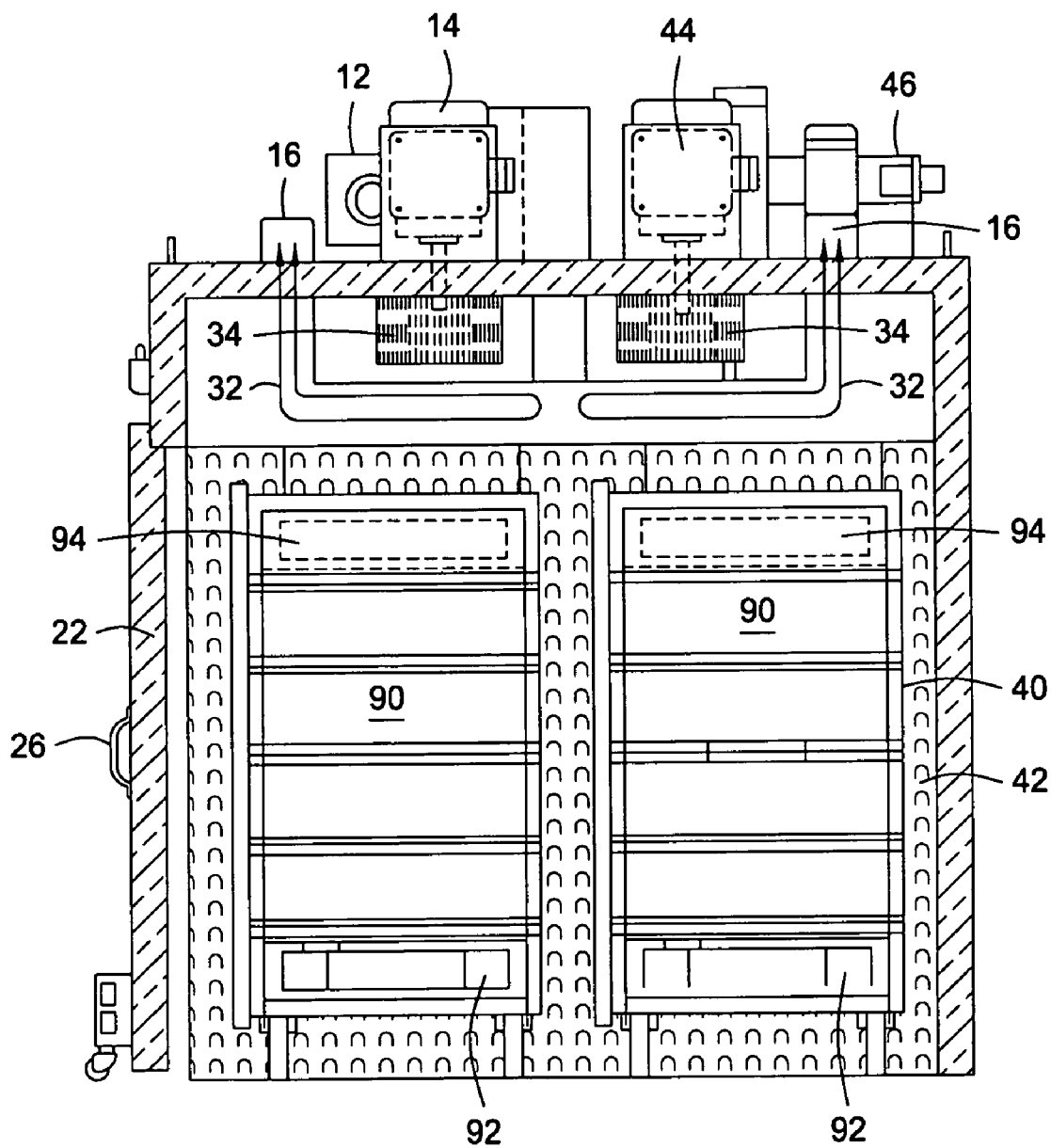
FIG. 4 is a side view of the sterilization system of FIG. 1.

In addition, the sterilization system 10 has an airflow outlet 28 connected to the exhaust filter box 44 (FIG. 3) and an airflow inlet 30 connected to the intake filter box 14 (FIG. 4). Another deflector 36b sets up a divider between the airflow outlet 28 and the airflow inlet 30.

FIG. 2 also illustrates the set up of the hot air circulating system. A re-circulating motor 18 is attached to a re-circulating blower 34. The re-circulating blower 34 is situated between a set of heaters 32 and the first and third plenum 38a, 38b (as discussed below).

FIG. 3 is another cutaway view of the sterilization system 10 showing the operation hot air flowing sterilizing a container 90. The intake slide duct 70 and the exhaust slide duct 80 penetrate the container 90 to allow air to flow in and out of the container.

In operation, air flow enters and exits through the intake filter box 14 and the exhaust filter box 44 of the sterilization system 10, respectively. As shown, the deflector 36b is positioned between the airflow inlet 30 and the airflow outlet 28. Air enters the sterilization system 10 through the airflow inlet 30 via the intake filter box 14. The intake airflow blower 12 (FIG. 4) pushes the air towards the heater 32 and the re-circulating blower 34, which is driven by the re-circulating motor 18. Air is heated while moving pass heater 32 and the deflectors 36a directs the air to go down either the first plenum 38a or the third plenum 38b.

Hot air traveling down the first plenum 38a enters the intake slide duct 70. The intake slide duct 70 having an air turning vane 72, which directs the hot air into the bottom of the container 90. Once inside the container 90, hot air circulates, heats up the internal area of the container, rises and exits through the top of the container 90 via the exhaust slide duct 80. Once exited from the container, the hot air is re-heated at the heater 32, and is re-circulated within the sterilization system 10.

Hot air can also travel down the third plenum 38b, wherein hot air will enter through the diffuser panels 42 of the semi-pierced duct wall 40. As shown in the diagram, hot air travels down the third plenum 38b and can enter through the diffuser panels 42 along the entire semi-pierced duct wall 40. Therefore, the hot air travels and sterilizes the outside of the container 90. In this case, the hot air aids the overall heating of the container 90 and in effect lower the overall heating/sterilization time of the container 90. Hot air then exits through the semi-pierced duct wall 40 or through the exhaust slide duct 80. The air is re-heated at the heater 32, and is re-circulated within the sterilization system 10.

Hot air may also exit along the deflector 36b, though the exhaust filter box 44 (FIG. 4) and the exhaust airflow blower 46 (FIG. 4). Approximately 90% of the air will re-circulate inside the sterilization system and 10% of air will exit from the sterilization system.

FIG. 4 is a side view of another embodiment of the sterilization system 10 illustrating the air intake and exhaust system. As discussed above, some systems can contain multiple filter boxes if necessary. As shown, an intake filter box 14 and exhaust filter box 44 are mounted on top of the sterilization system 10, each having a respective airflow blower, intake airflow blower 12 and exhaust airflow blower 46. Two re-circulating blowers 34 and two sets of heaters 32 are situated inside the sterilization system 10. The heaters 32 are connected to the electrical junction box 16, each with electrical communication with airflow switches (not shown).

In another embodiment, the sterilization system 10 is capable of sterilizing two containers 90. Each container 90 having an intake cover panel 92 at the bottom and an exhaust cover panel 94 at the top, such that the intake slide duct 70 penetrates the container 90 through the intake cover panel 92 and the exhaust slide duct 80 penetrates the container 90 through the exhaust cover panel 94. Furthermore, the container 90 can be open cages, partially sealed containers, or substantially sealed containers. In each case, the plenums 38a, b, c, the intake slide duct 70 and the exhaust slide duct 80 can facilitate the sterilization of the container 90 in more effective and efficiency manner.

The safety airflow switches (not shown) are sensors that can shut down the heaters 32 (FIG. 3) if they sense that there is no air flowing over the heaters 32. The safety airflow switches are pressure differential switches; they measure airflow of the air intake and the air outlet. For example, if the blowers 12, 34, 46 are not functioning and the air is not moving, the safety airflow switches will shut down the heaters 32 to prevent the system 10 from overheating.

Figure 5:
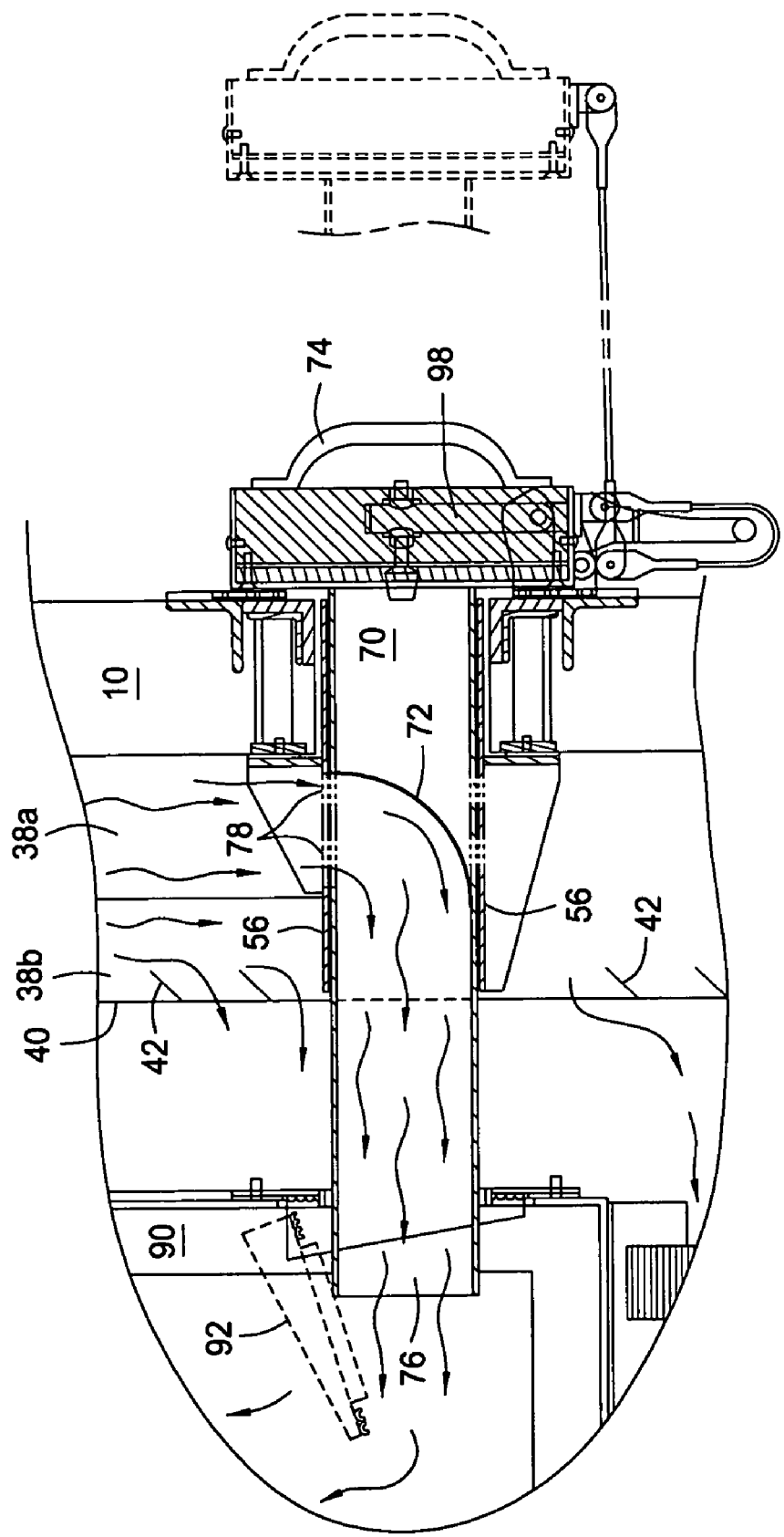
FIG. 5 is a detail view of an intake slide duct penetrating the sterilization system according to an embodiment of the invention.

FIG. 5 is a detail view of the intake slide duct 70 penetrating the sterilization system 10 according to an embodiment of the invention. As shown in the diagram, the intake slide duct 70 also penetrates the first plenum 38a and the third plenum 38b into the chamber 102 of the sterilization system 10 and further into the container 90 through the intake cover panel 92. Clamps 98 keep the intake slide duct in position while hot air circulates inside the chamber 102 and the container 90. The container 90 can be removed from the sterilization system 10 when the intake slide duct 70 is disengaged from the container 90.

The intake slide duct 70 is an elongated duct having a handle 74 on one end and an opening 76 at the other end. The intake slide duct 70 also has an air turning vane 72 within the elongated duct which can direct air flow. The elongated duct 70 is substantially adjacent to the slide base 56 of the sterilization system 10. The top of the intake slide duct and the slide base 56 having apertures 78 to allow hot air to enter into the elongated duct. Hot air travels through the elongated duct and enter into the container 90 through the opening 76. Furthermore, hot air can also travel through the third plenum 38b, through the diffuser panels 42 of the semi-pierced duct wall 40 to sterilize the external surface of the container 90.

Figure 6:
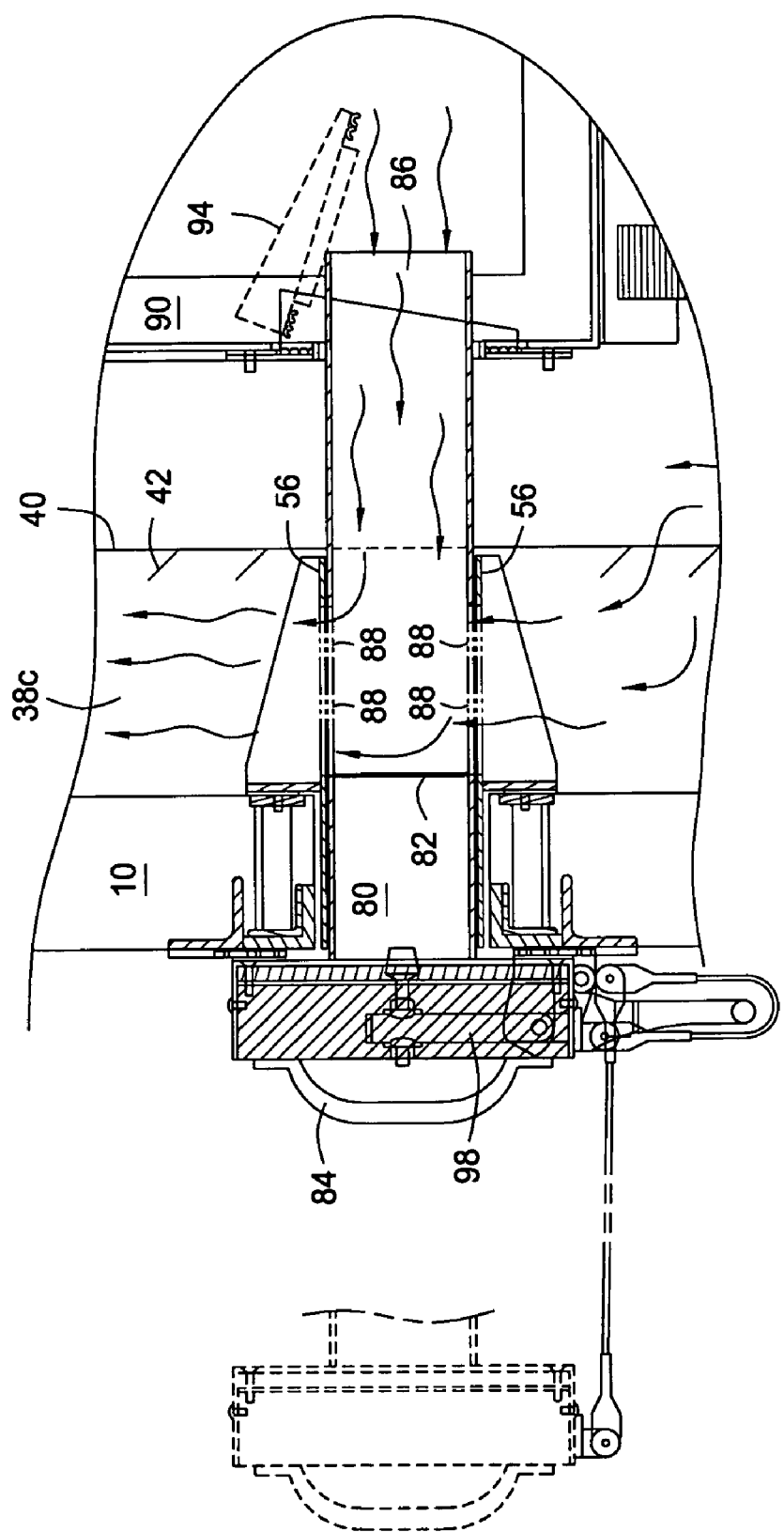
FIG. 6 is a detail view of an exhaust slide duct penetrating the sterilization system according to an embodiment of the invention.

FIG. 6 is a detail view of an exhaust slide duct 80 penetrating the sterilization system according to an embodiment of the invention. As shown in the diagram, the exhaust slide duct 80 also penetrates the second plenum 38c into the chamber 102 of the sterilization system 10 and further into the container 90 through the exhaust cover panel 94. Clamps (not shown) keep the exhaust slide duct in position while hot air circulates inside the chamber 102 and the container 90. The container 90 can be removed from the sterilization system 10 when the exhaust slide duct 80 is disengaged from the container 90.

The exhaust slide duct 80 is an elongated duct having a handle 84 on one end and an opening 86 at the other end. The exhaust slide duct 80 also has an air turning vane 82 within the elongated duct which can direct air flow. The elongated duct 80 is substantially adjacent to the slide base 56 of the sterilization system 10. The top and bottom of the exhaust slide duct 80 and the slide base 56 having apertures 88. Hot air exits the container 90 through the opening 86 and travels through the elongated duct and exits through the top apertures 88 and into the chamber 102 of the sterilization system 10. Furthermore, hot air may also travel through the second plenum 38c, through diffuser panels 42 of the semi-pierced duct wall 40, through the bottom and top apertures 88 and into the chamber 102 of the sterilization system 10.

In operation, there are three cycles to the sterilization process: ramping, heating and cooling. In the ramping process, the chamber 102 will increase heat from ambient temperature to a set point temperature, which is typically about 300° F. The length of time it takes to ramp the temperature to 300° F. depends on the load in the chamber 102 and the ambient temperature in the system. Typically, the target time is between 30 to 40 minutes. The recirculation blower is sized to deliver a predetermined volume air to the sterilizing process at a static pressure in the range of 1" water column.

Typically, the user will run test to determine the time it takes to heat up the chamber 102 before the actual sterilization process. The user will locate the coolest spot in the chamber 102 and place a test strip in that spot and determine the time it takes the coolest spot to reach the desired temperature.

Then, there is a pre-determined soak period at the set point temperature. During this period, hot air will circulate within the system and sterilize the content for the predetermined time period.

When the cycle is over, the sterilization system will cool down the system as rapidly as possible. This is when the intake and exhaust volume increase to try to extract the heat out of the box. In the cooling process, the system will cool down to about 140° F. At that temperature, operators can safely handle the load in the chamber 102 without getting burned.

In the present embodiment, the container is made with stainless steel, carbon steel, or other suitable metals to be used for a dry heat sterilization system. Furthermore, this sterilization system can be used to sterilize animal cages that are used for housing rodents, canines, poultries, and mammals. In the alternative, the sterilization system may also be used for sterilizing biological or chemical contaminants.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A sterilization system using hot air, comprising:
   (a) a housing having a first wall with an airflow inlet and an airflow outlet, a second wall coupled to the first wall, and a third wall coupled to the first wall, such that a chamber is formed by the first, second, and third walls;
   (b) a first plenum substantially adjacent to the second wall;
   (c) a second plenum substantially adjacent to the third wall;
   (d) a filter box mounted on the first wall;
   (e) an intake air blower coupled to the filter box and mounted on the first wall;
   (f) a heater mounted inside the chamber and adjacent to an airflow inlet;
   (g) an intake slide duct slidably attached to the second wall, such that the intake slide duct penetrates through the second wall, the first plenum, and into the chamber; and
   (h) an exhaust slide duct slidably attached to the third wall, such that the exhaust slide duct penetrates through the third wall, the second plenum, and into the chamber.

2. The sterilization system of claim 1, further comprising a third plenum substantially adjacent to the first plenum.

3. The sterilization system of claim 2, further comprising a deflector mounted inside the chamber, such that the deflector directs air between the first and third plenums.

4. The sterilization system of claim 1, further comprising semi-pierced duct walls mounted inside the chamber, such that the intake slide duct and the exhaust slide duct penetrate through the semi-pierced duct walls.

5. The sterilization system of claim 4, wherein the semi-pierced duct walls further comprises adjustable diffuser panels.

6. The sterilization system of claim 1, wherein the intake slide duct further comprises an opening at an end of the intake slide duct, an air turning vane, and apertures on the top of the slide duct, such that when air enters from the top of the intake slide duct, the air turning vane guides the airflow, thereby the air enters into the chamber through the opening.

7. The sterilization system of claim 1, wherein the exhaust slide duct further comprises an opening at an end of the exhaust slide duct and apertures on both top and bottom of the exhaust slide duct, such that air can enter into the exhaust slide duct from the opening or the bottom apertures and exit through the top apertures.

8. The sterilization system of claim 1, wherein the intake slide duct is relatively lower than the exhaust slide duct, thereby hot air enters through the intake slide duct, rises to the top of the chamber and exits through the exhaust slide duct.

9. The sterilization system of claim 1, wherein the filter box is an intake filter box, an exhaust filter box, or a combination thereof.

10. The sterilization system of claim 9, wherein the intake air blower directs air to flow from the intake filter box through the airflow inlet and into the chamber.

11. The sterilization system of claim 1, further comprises an exhaust air blower coupled to the filter box, wherein the filter box is an exhaust filter box or combination intake and exhaust filter box, and mounted on the first wall, wherein the exhaust air blower directs air to flow from the chamber through the airflow outlet and into the filter box.

12. The sterilization system of claim 1, further comprises a re-circulating air blower mounted under the first wall and inside the chamber to re-circulate air.

13. The sterilization system of claim 12, wherein the heater is mounted between the airflow inlet and the re-circulating air blower, such that the air is heated when it enters the re-circulating air blower from the airflow inlet.

14. The sterilization system of claim 1, further comprising:
   the intake slide duct further comprises an intake opening at an end of the intake slide duct, an air turning vane, and intake apertures on the top of the intake slide duct, such that when air enters from the top of the intake slide duct, the air turning vane guides the airflow, thereby the air enters into the chamber through the intake opening; and the exhaust slide duct further comprises an exhaust opening at an end of the exhaust slide duct and exhaust apertures on both top and bottom of the exhaust slide duct, such that air can enter into the exhaust slide duct from the exhaust opening or the bottom exhaust apertures and exit through the exhaust top apertures.

15. The sterilization system of claim 14, wherein the intake slide duct is relatively lower than the exhaust slide duct, thereby hot air enters through the intake slide duct, rises to the top of the chamber and exits through the exhaust slide duct.

16. An apparatus for sterilization using air, comprising:
(a) a housing means having a first wall means with an airflow inlet and an airflow outlet, a second wall means coupled to the first wall means, and a third wall means coupled to the first wall means, such that a chamber means is formed by the first, second, and third walls means;
(b) a first airflow means substantially adjacent to the second wall means;
(c) a second airflow means substantially adjacent to the third wall means;
(d) a filtering means mounted on the first wall means;
(e) an air intake means coupled to the filtering means and mounted on the first wall means;
(f) a heating means mounted adjacent to an airflow inlet means;
(g) a first air directing means slidably attached to the second wall means, such that the first air directing means penetrates through the second wall means, the first airflow means, and into the chamber means; and
(h) a second air directing means slidably attached to the third wall means, such that the second air directing means penetrates through the third wall means, the second airflow means, and into the chamber means.

17. The apparatus of claim 16, further comprising: a third airflow means substantially adjacent to the first airflow means.

18. The apparatus of claim 17, further comprising: a deflecting means mounted inside the chamber means, such that the deflecting means deflects air between the first and third airflow means.

19. The apparatus of claim 16, further comprising semi-pierced barrier means mounted inside the chamber means, such that the first air directing means and the second air directing means penetrate through the semi-pierced barrier means.

20. The apparatus of claim 19, wherein the semi-pierced barrier means further comprises adjustable diffuser panels means.

21. The apparatus of claim 16, wherein the first air directing means further comprises an opening at the end, an air turning vane, and apertures on the top of the first air directing means, such that when air enters from the top, the air turning vane guides airflow, thereby the air enters into the chamber through the opening.

22. The apparatus of claim 21, wherein the second air directing means further comprises an opening and apertures on both top and bottom of the air directing-means, such that air can enter from the opening or the bottom apertures and exit through the top apertures.

23. The apparatus of claim 22, wherein the first air directing means is relatively lower than the second air directing means, thereby hot air entering through the first directing means, rising to the top of the chamber and exiting through the second air directing means.

* * * * *